US011673969B2

(12) United States Patent
Li et al.

(10) Patent No.: US 11,673,969 B2
(45) Date of Patent: Jun. 13, 2023

(54) ANTI-BIOTIN ANTIBODY AND APPLICATION THEREOF

(71) Applicant: HANGZHOU BIOLYNX TECHNOLOGY CO., LTD., Zhejiang (CN)

(72) Inventors: Mingzhen Li, Zhejiang (CN); Li Pan, Zhejiang (CN); Min Hu, Zhejiang (CN); Hao Liu, Zhejiang (CN)

(73) Assignee: HANGZHOU BIOLYNX TECHNOLOGY CO., LTD., Zhejiang (CN)

(*) Notice: Subject to any disclaimer, the term of this patent is extended or adjusted under 35 U.S.C. 154(b) by 0 days.

(21) Appl. No.: 17/436,744

(22) PCT Filed: Sep. 4, 2020

(86) PCT No.: PCT/CN2020/113475
§ 371 (c)(1),
(2) Date: Sep. 7, 2021

(87) PCT Pub. No.: WO2021/169233
PCT Pub. Date: Sep. 2, 2021

(65) Prior Publication Data
US 2022/0041755 A1  Feb. 10, 2022

(30) Foreign Application Priority Data

Feb. 25, 2020 (CN) .......................... 202010115961.2

(51) Int. Cl.
| | |
|---|---|
| *G01N 31/00* | (2006.01) |
| *G01N 33/53* | (2006.01) |
| *C07K 16/44* | (2006.01) |
| *G01N 33/577* | (2006.01) |

(52) U.S. Cl.
CPC ........... *C07K 16/44* (2013.01); *G01N 33/577* (2013.01)

(58) Field of Classification Search
None
See application file for complete search history.

(56) References Cited

FOREIGN PATENT DOCUMENTS

| CN | 104411725 A | 3/2015 | |
|---|---|---|---|
| CN | 111171154 A | 5/2020 | |
| WO | WO-00/50088 A2 | 8/2000 | |
| WO | WO-2020/028776 A1 | 2/2020 | |
| WO | WO-2020028776 A1 * | 2/2020 | ............. C07K 16/44 |

OTHER PUBLICATIONS

Absolute Antibody, Anti-Biotin [mAb2] data sheet, 2021 (Year: 2021).*
Chen, Shou-hui et al., "Study of Interaction Between Biotin and Its Monoclonal Antibody by Surface Plasma Resonance (SPR)", Chinese Journal of Applied Chemistry, vol. 21, Issue No. 3, Mar. 31, 2004, pp. 266-270.
Papasarantos, Ilias et al., "Solid-Phase Synthesis of a Biotin Derivative and its Application to the Development of Anti-Biotin Antibodies", Applied Biochemistry Biotechnology, vol. 162, Dec. 1, 2009, pp. 221-232.
Berger, Melvin, "Production of antibodies that bind biotin and inhibit biotin containing enzymes," Biochemistry, vol. 14, Issue No. 11, Jun. 1, 1975, pp. 2338-2342.
Dakshinamurti et al. "Production and characterization of a monoclonal antibody to biotin," Biochemical Journal, vol. 237, Issue No. 2, Jul. 1, 1986, pp. 477-482.
Bagci, H. et al. "Monoclonal anti-biotin antibodies simulate avidin m the recognition of biotin," FEBS Letters, Elsevier, Amsterdam, NL, vol. 322, Issue No. 1, May 3, 1993, pp. 47-50.
Kohen, F. et al. "Preparation and properties of anti-biotin antibodies," Methods Enzymol. 1997, vol. 279, pp. 451-463.
Cao, Y. et al. "Development of a bispecific monoclonal antibody as a universal immunoprobe for detecting biotinylated macromolecule," Journal Of Immunological Methods, Elsevier Science Publishers B.V., Amsterdam, NL, vol. 220, Issue No. 1-2, Nov. 1, 1998, pp. 85-91.
Vincent, P. et al., "A comparison of the binding of biotin and biotinylated macromolecular ligands to an anti-biotin monoclonal antibody and to streptavidin", Journal of Immunological Methods, vol. 165, Dec. 31, 1993, pp. 177-182.

* cited by examiner

*Primary Examiner* — Lisa V Cook
(74) *Attorney, Agent, or Firm* — Muncy, Geissler, Olds & Lowe, P.C.

(57) ABSTRACT

The present disclosure provides an anti-biotin antibody, and provides an amino acid sequence encoding the CDRs of the antibody. Studies have shown that the antibody only reacts with a biotin conjugate or derivative, and does not react with free biotin. The present disclosure further provides applications of the antibody in, including but not limited to, ELISA, cell capture, sorting and enrichment, western blotting, flow cytometry, immunocytofluorescent staining, and immunohistochemistry. The anti-biotin antibody conjugated immunomagnetic beads can specifically and directly recognize a biotin labeled antigen, and do not bind to free biotin which is often presented in clinical samples and culture media. In addition, the anti-biotin antibody-conjugated magnetic beads or anti-biotin antibody-fluorescein provide an ideal solution for the isolation of specific cells, and can even enrich and separate target cells from samples rich in debris or other rare biological materials.

2 Claims, 5 Drawing Sheets
Specification includes a Sequence Listing.

US 11,673,969 B2

SEQUENCE LISTING

```
<160> NUMBER OF SEQ ID NOS: 6

<210> SEQ ID NO 1
<211> LENGTH: 6
<212> TYPE: PRT
<213> ORGANISM: Artificial Sequence
<220> FEATURE:
<223> OTHER INFORMATION: Synthesized

<400> SEQUENCE: 1

Ser Ser Tyr Trp Ile Cys
1               5

<210> SEQ ID NO 2
<211> LENGTH: 18
<212> TYPE: PRT
<213> ORGANISM: Artificial Sequence
<220> FEATURE:
<223> OTHER INFORMATION: Synthesized
```

```
<400> SEQUENCE: 2

Cys Ile Asp Ala Gly Ser Ser Gly Ser Thr Tyr Tyr Ala Arg Trp Val
1               5                   10                  15

Asn Gly

<210> SEQ ID NO 3
<211> LENGTH: 14
<212> TYPE: PRT
<213> ORGANISM: Artificial Sequence
<220> FEATURE:
<223> OTHER INFORMATION: Synthesized

<400> SEQUENCE: 3

Glu Gly Asp Trp Gly Ala Pro Ile Tyr Tyr Gly Val Asp Leu
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthesized

<400> SEQUENCE: 4

Gln Ser Ser Gln Ser Val Tyr Asn Asn Asn Gln Leu Ser
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthesized

<400> SEQUENCE: 5

Tyr Ala Ser Thr Leu Ala Ser
1               5

<210> SEQ ID NO 6
<211> LENGTH: 12
<212> TYPE: PRT
<213> ORGANISM: Artificial Sequence
<220> FEATURE:
<223> OTHER INFORMATION: Synthesized

<400> SEQUENCE: 6

Leu Gly Gly Tyr Tyr Asp Tyr Ala Asp Thr Ser Ala
1               5                   10
```

ANTI-BIOTIN ANTIBODY AND APPLICATION THEREOF

TECHNICAL FIELD

The present disclosure belongs to the field of biotechnology, and more specifically, the present disclosure relates to an anti-biotin antibody and application thereof.

BACKGROUND ART

Biotin is a member of the water-soluble vitamin B family, also known as vitamin H, D-biotin, vitamin B7, Coenzyme R and the like, with a molecular weight of 244.31. Biotin is a colorless long needle-like crystal, with a fused ring of urea and thiophene, and a valeric acid side chain. Biotin is very slightly soluble in water (22 mg/100 ml water, 25° C.) and ethanol (80 mg/100 ml, 25° C.), soluble in hot water and dilute lye, and insoluble in other common organic solvents. Biotin decomposes in strong alkali or oxidants.

In scientific research fields such as biological sciences, biotin is often used as a label to provide a reaction target for immobilization or coloration and the like. In order to facilitate labeling, biotin is usually made into derivatives, such as biotin-hydroxy succinimide (BNHS), by chemical methods, so the derivatives can easily form biotinylated products with various types of large and small molecules such as proteins, carbohydrates and enzymes, and can be detected by the binding of avidin. Biotin-Avidin-System (BAS) is a new type of biological reaction amplification system developed in the late 1970s. Although the binding between avidin and biotin is not an immune reaction, the binding has strong specificity and high affinity. Once the avidin and biotin are bound, the binding is extremely stable. Since one avidin molecule has 4 binding sites for biotin molecules, more biotinylated molecules can be connected to form a complex similar to a crystal lattice. A large number of studies in recent years have confirmed that the biotin-avidin system has been successfully being used in various labeling applications. The strong binding with high affinity between the biotin and avidin and a multi-stage amplification effect can greatly improve the sensitivity of detection and analysis, so that BAS is soon widely applied to biology, diagnosis, medicine and other fields. Although the biotin-avidin detection system has the above advantages, the binding between the biotin and avidin is non-specific. Avidin can recognize biotin of all origins and forms, including biotin derivatives and free biotin molecules. Therefore, it is necessary to purify derivatives and conjugates in practical application, otherwise serious non-specific signals will be generated, and further affect the sensitivity and accuracy of detection.

Antibodies are large Y-shaped proteins secreted by plasma cells (effector B cells), and used by the immune system to identify and neutralize foreign substances such as bacteria and viruses. Antibodies can recognize a unique feature of a specific foreign object, and the foreign object is called an antigen. Antibodies have a symmetrical structure with 4 polypeptide chains, of which 2 longer are the same heavy chains (H chain) with a relatively larger molecular weight, and 2 shorter are the same light chains (L chain) with a relatively smaller molecular weight. The whole antibody molecule can be divided into two parts, namely a constant region and a variable region. The variable region of an antibody is respectively composed of 4 framework regions (FR) and 3 highly variable antigen complementary determinant regions (CDR), where the CDRs are specific binding sites of the antibody. The FRs of different antibody molecules all have the same or almost the same amino acid sequence. The variable regions are located at the two arms of "Y". In the variable regions, a small part of amino acid residues changes at high frequency. The composition and sequence of these amino acid residues are more prone to variation, so the regions are called the variable regions. The variable regions are located on the surface of the molecule and consist of up to 17 amino acid residues, and as few as 2-3 amino acid residues. The amino acid sequences of the variable regions determine the specificity of the antibody binding antigens. Two antigen binding sites on an antibody molecule are the same, located at the two arms, and called antigen-binding fragments (Fab). The handle of "Y" is called crystalline fragment (Fc), and carbohydrates are bound to Fc.

Antibody fragments are fragments formed by protease hydrolysis of antibodies. For example, papain digests IgG to form two identical Fab fragments and one Fc fragment; pepsin digests IgG to form one F(ab')2 fragment and several polypeptide fragments (pFc'). If the disulfide bond between the heavy chains of F(ab')2 is broken, two Fab fragments can be formed, and the Fab fragments can be further enzymatically digested into Fv fragments. The antigen-binding fragments have the forms of full-length antibody (such as IgG), Fab, F(ab')2, scFv and the like.

Kohen, F. et al. reported preparation and characteristics of anti-biotin antibodies (Methods Enzymol. 279 (1997) 451-463). Bagci, H. et al. (FEBS Lett. 322 (1993) 47-50) reported simulated affinity of monoclonal anti-biotin antibodies in recognizing biotin. Cao, Y. et al. reported development of bispecific monoclonal antibodies as universal immunoprobes for detection of biotinylated macromolecules (J. Immunol. Meth. 220 (1998) 85-91). Dakshinamurti et al. reported production and characterization of monoclonal antibodies against biotin (Biochem. J. 237 (1986) 477-482). Vincent, P. et al. (J. Immunol. Meth. 165 (1993) 177-182) reported comparison of binding between biotin and biotinylated macromolecular ligands with binding between anti-biotin monoclonal antibodies and streptavidin. Berger, M. et al. (Biochem. 14 (1975) 2338-2342) reported production of antibodies that bind biotin and inhibit biotin-containing enzymes.

At present, anti-biotin antibodies on the market bind equally to free biotin and biotin derivatives, which is similar to the biotin-avidin system. There are few antibodies that can only bind to biotin derivatives. Antibodies that bind equally to free biotin and biotin derivatives can also detect free biotin in a sample. The objective of the present disclosure is to obtain an antibody that does not react with free biotin but specifically recognizes the biotin conjugates or derivatives, which can be used in various immunoassays without the interference of free biotin.

SUMMARY OF THE DISCLOSURE

The present disclosure provides an anti-biotin antibody or an antibody fragment thereof, and provides an amino acid sequence encoding the CDR regions of the antibody. The antibody only reacts with a biotin conjugates or derivatives, and does not react with free biotin. The present disclosure further provides applications of the antibody in, including but not limited to, ELISA, B cell cloning by magnetic bead method, western blotting, flow cytometry, immunocytofluorescent staining, and immunohistochemistry.

The present disclosure provides the following technical solutions: an anti-biotin antibody, the antibody uses a Kabat method to analyze CDR-H1, CDR-H2, CDR-H3, CDR-L1, CDR-L2 and CDR-L3 including the following polypeptide sequences:

(1) CDR-H1 including at least 6 amino acid sequences of SEQ ID NO: 1, the sequence being SSYWIC;

(2) CDR-H2 including at least 18 amino acid sequences of SEQ ID NO: 2, the sequence being CIDAGSSGSTYYARWVNG;

(3) CDR-H3 including at least 14 amino acid sequences of SEQ ID NO: 3, the sequence being EGDWGAPIYYGVDL;

(4) CDR-L1 including at least 13 amino acid sequences of SEQ ID NO: 4, the sequence being QSSQSVYNNNQLS;

(5) CDR-L2 including at least 7 amino acid sequences of SEQ ID NO: 5, the sequence being YASTLAS;

(6) CDR-L3 including at least 12 amino acid sequences of SEQ ID NO: 6, the sequence being LGGYYDYADTSA, where, the anti-biotin antibody specifically binds to non-free biotin.

Preferably, the antibody is a rabbit monoclonal antibody.

The present disclosure further provides another technical solution: applications of the anti-biotin antibody in, including but not limited to, ELISA, cell capture, sorting and enrichment, western blotting, flow cytometry, immunocytofluorescent staining and immunohistochemistry.

Advantages and effects of the present disclosure:

1. The anti-biotin antibody conjugated immunomagnetic beads can specifically and directly recognize a biotin labeled antigen, and do not bind to free biotin which is often presented in clinical samples and culture media. The anti-biotin antibody-conjugated magnetic beads in the experiment have the advantage of not binding to free biotin, and can provide the most effective labeling and cell isolation based on the feature. The anti-biotin antibody-conjugated magnetic beads or anti-biotin antibody-fluorescein conjugates provide an ideal solution for the isolation of specific cells, and can even enrich and isolate target cells from samples rich in debris or other rare biological materials.

2. The quality of the anti-biotin monoclonal antibody provided by the present disclosure has great controllability and repeatability, so the anti-biotin antibody can provide a good bias for further establishment and application of more specific and sensitive immunoassays based on the preliminary analysis and identification on the characteristics of the obtained antibody.

3. In addition to the application of B cell cloning, the present disclosure can also be used in application in various immunoassays, such as ELISA, western blotting, flow cytometry sorting and detection, immunocytofluorescent staining, immunohistochemistry, and enrichment and detection of rare cells in clinical samples, and has broad application prospects.

DETAILED DESCRIPTION OF THE DISCLOSURE

The present disclosure is further described by the examples, but the present disclosure is not limited to the examples, nor can the examples be construed as limitations of the present disclosure.

Example 1

An anti-biotin antibody disclosed in the technical solution is a rabbit monoclonal antibody. The antibody uses a Kabat method to analyze CDR-H1, CDR-H2, CDR-H3, CDR-L1, CDR-L2 and CDR-L3 including the following polypeptide sequences:

(1) CDR-H1 including at least 6 amino acid sequences of SEQ ID NO: 1, the sequence being SSYWIC;

(2) CDR-H2 comprising at least 18 amino acid sequences of SEQ ID NO: 2, the sequence being CIDAGSSGSTYYARWVNG;

(3) CDR-H3 comprising at least 14 amino acid sequences of SEQ ID NO: 3, the sequence being EGDWGAPIYYGVDL;

(4) CDR-L1 comprising at least 13 amino acid sequences of SEQ ID NO: 4, the sequence being QSSQSVYNNNQLS;

(5) CDR-L2 comprising at least 7 amino acid sequences of SEQ ID NO: 5, the sequence being YASTLAS; and (6) CDR-L3 comprising at least 12 amino acid sequences of SEQ ID NO: 6, the sequence being LGGYYDYADTSA.

The anti-biotin antibody specifically binds to non-free biotin.

The following Examples 2-8 are applications of the antibody in, including but not limited to, ELISA, B cell cloning by magnetic bead method, western blotting, flow cytometry, immunocytofluorescent staining, and immunohistochemistry.

The antibody can recognize the biotin motif of a protein-biotin conjugation complex coated on an ELISA plate by an indirect ELISA method; and the antibody does not recognize free biotins in an indirect competitive ELISA method.

Example 2: Direct Recognition of Biotin Labeled Antigens

A biotin conjugate biotin-X was diluted to a suitable concentration, e.g., 1 µg/mL. An ELISA plate was coated with the biotin conjugate biotin-X, sealed with a sealing film, and incubated at 4° C. overnight.

The next day, the ELISA plate was placed on a plate washer, washed with PBST 3 times, and blocked with skimmed milk or a BSA blocking buffer. The ELISA plate was incubated on a shaker at 30° C. for 1 about h.

The anti-biotin antibody was pre-diluted to a suitable concentration, e.g., 1 µg/mL. Then serial dilution was made by 8 times. After block, the plate was washed 3 times. 50 µL of diluted anti-biotin antibody was added to each well. The plate was incubated at 30° C. on a shaker for about 1 h.

After the plate was washed, 50 μL of HRP-conjugated goat anti-rabbit IgG secondary antibody was added to each well. The plate was incubated at 30° C. on a shaker for about 45 min.

After the plate was washed, 50 μL of TMB was added to each well. The plate was kept at 30° C. in dark for coloration on a shaker for about 15 min.

50 μL of $H_2SO_4$ stop solution was added to stop the reaction, and the absorbance was read on a microplate reader after about 5-30 min.

Figure 1:
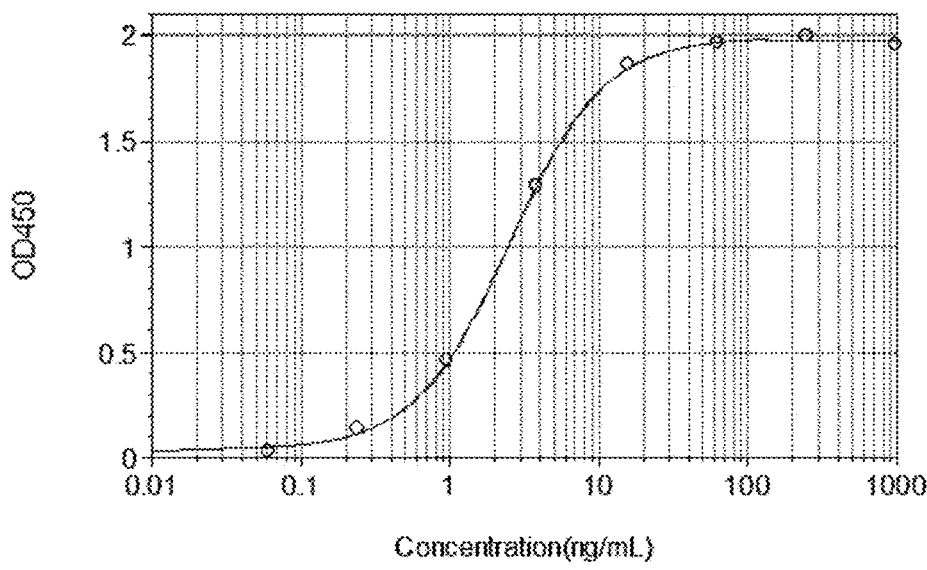
FIG. 1 is a picture of indirect ELISA results of an anti-biotin antibody.

The concentration of the anti-biotin antibody was taken as the abscissa and the OD value was taken as the ordinate to make a four-parameter fitting curve (as shown in FIG. 1), and the EC50 (i.e., the half effective concentration) value of the antibody was determined as 2.52 ng/mL. Therefore, the ELISA sensitivity of the antibody against the biotin-X antigen is 2.52 ng/mL.

Example 3: Specificity to Biotin Labeled Antigens without Reaction with Free Biotin A biotin conjugate biotin-X was diluted to a suitable concentration, e.g., 1 μg/mL. An ELISA plate was coated with the biotin conjugate biotin-X, sealed with a sealing film, and incubated at 4° C. overnight.

The next day, the ELISA plate was placed on a plate washer, washed with PBST 3 times, and blocked with skimmed milk or a BSA blocking buffer. The ELISA plate was incubated on a shaker at 30° C. for 1 h.

The anti-biotin antibody was pre-diluted to an appropriate concentration for use. Free molecules of biotin were pre-adjusted to a suitable starting concentration. Then serial dilution was made by 10 times. 50 μL of the anti-biotin antibody and 50 μL of the diluted free molecules of biotin were mixed on another clean dilution plate. Then the plate was incubated at 30° C. and 100 rpm on a shaker for about 30 min.

After the ELISA plate was washed, 50 μL of the mixture in step (3) was added to each well. The plate was incubated at 30° C. on a shaker for about 1 h.

After the plate was washed, 50 μL of HRP-conjugated goat anti-rabbit IgG secondary antibody was added to each well. The plate was incubated at 30° C. on a shaker for about 45 min.

After the plate was washed, 50 μL of TMB was added to each well. The plate was kept at 30° C. in dark for coloration on a shaker for about 15 min.

50 μL of $H_2SO_4$ stop solution was added to stop the reaction, and the absorbance was read on a microplate reader after about 5-30 min.

Figure 2:
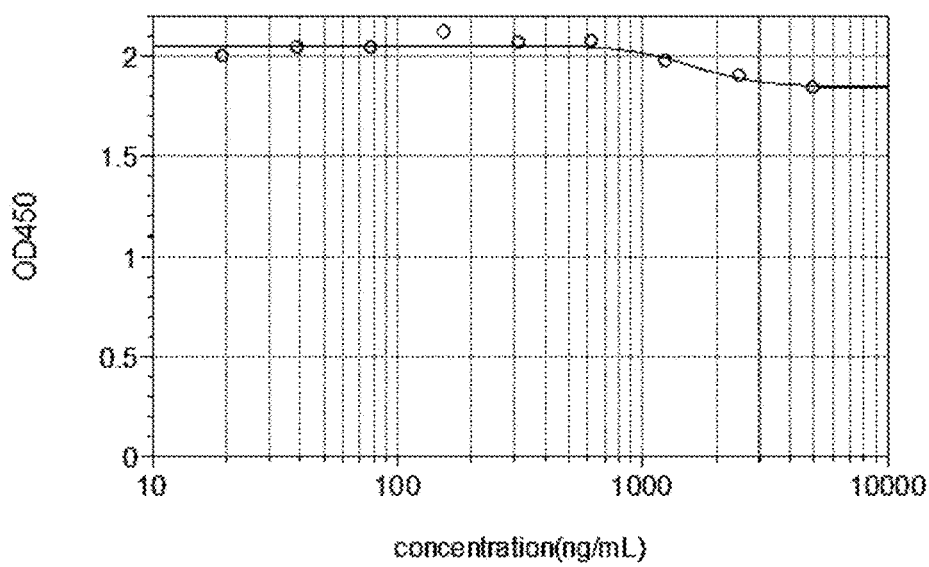
FIG. 2 is a picture of indirect competitive ELISA results of an anti-biotin antibody.

According to FIG. 2, the absorbance basically does not change after the addition of the free biotin at different concentrations. It can be seen that the addition of free biotin does not affect the binding of the antibody to the biotin conjugate biotin-X, which shows that the antibody only binds to conjugated biotin, while does not bind to free biotin. the anti-biotin antibody shows very good specificity.

Example 4: Cell Capture, Sorting and Enrichment, and Monoclonal Antibody Preparation Cell capture and sorting include but are not limited to a magnetic bead method and a flow cytometry method.

Figure 3:
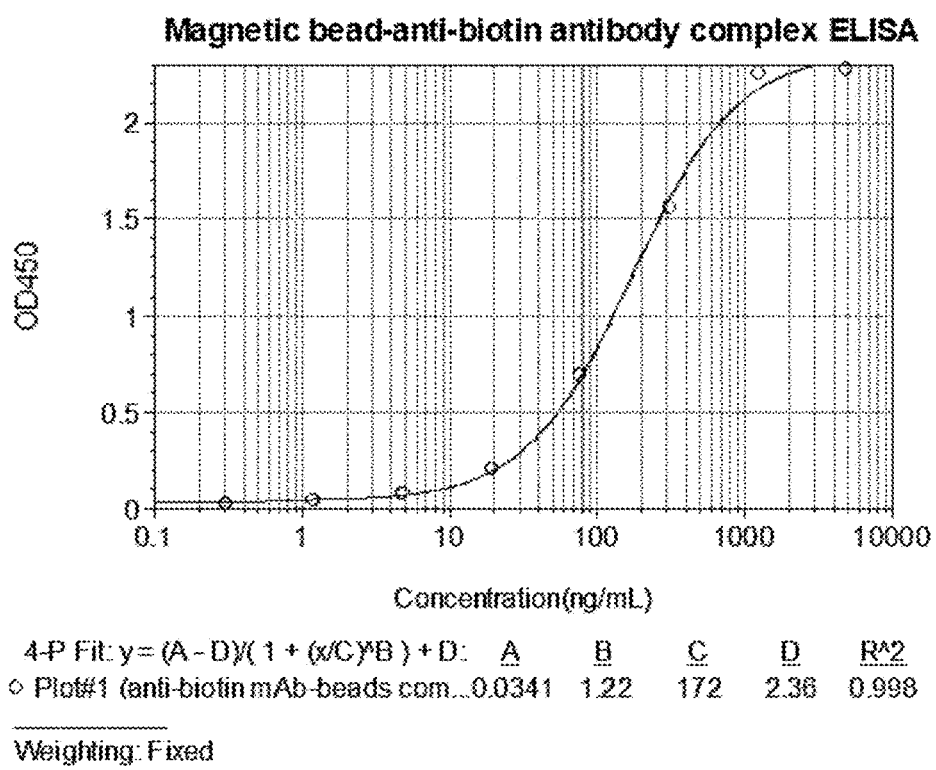
FIG. 3 is a picture of indirect ELISA results of an anti-biotin antibody-conjugated magnetic bead complex.

The embodiments of cell capture, sorting and enrichment, and monoclonal antibody preparation by the magnetic bead method are as follows:

The anti-biotin antibody was cross-linked to immunomagnetic beads to obtain anti-biotin antibody-immunomagnetic beads. After ELISA, as shown in FIG. 3, the antibody activity remains the same as before conjugation. After being filtered with a 0.45 μm filter membrane, the anti-biotin antibody-immunomagnetic beads were stored at 4° C. for later use.

Biotin was cross-linked to a peptide or a protein in a proper way to obtain a biotinylated polypeptide/protein complex (biotin-Y). The biotinylated polypeptide/protein complex (biotin-Y) was filtered with a 0.22 μM filter membrane and stored at −20° C. for later use.

Lymphocytes from animals immunized with antigen Y were taken, and the biotin-Y complex was added. The lymphocytes were incubated at 4-37° C. for 1-120 min, or a longer time accordingly, cells were washed with DPBS or a culture medium several times, and the supernatant was removed by centrifugation.

The washed cells were resuspended in DPBS or the culture medium, and a certain number of immunomagnetic beads were added and mixed at 4-37° C. for about 1-120 min, or a longer time accordingly.

After the incubation, the sample was applied to a magnetic field, and the magnetic bead-anti-biotin antibody-biotin-cell complex was enriched at the bottom. The supernatant was pipetted and discarded, then the magnetic field was removed. DPBS or the culture medium was added to wash the cells several times. Then a complete culture medium was added to resuspend the cells.

After the cells were counted, the cells were adjusted to a suitable concentration and inoculated into a cell culture plate or culture dish, and the cell culture plate or culture dish was supplemented with sufficient culture medium.

The cells were cultured for several days and then the supernatant was taken for detection.

Figure 4:
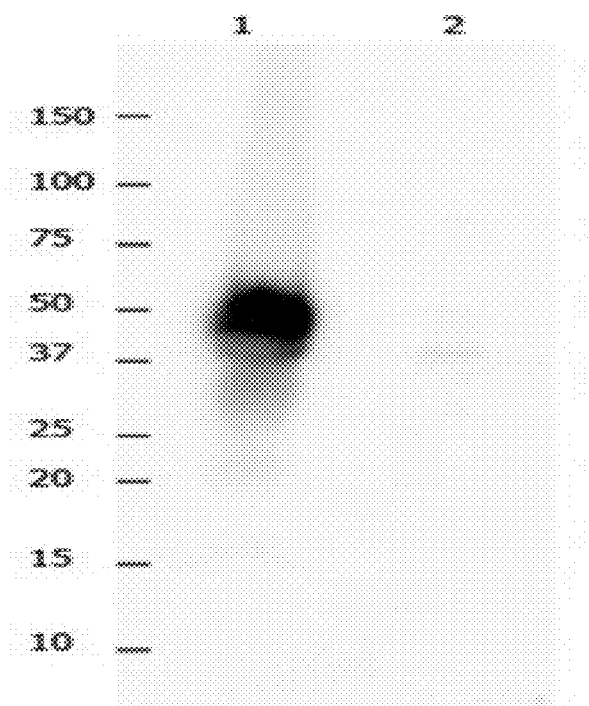
FIG. 4 is a picture of western blotting results of an anti-PD-L1 monoclonal antibody against NCI-H226 positive cell lysate and MCF-7 negative cell lysate, obtained by anti-biotin antibody conjugated immunomagnetic beads capture, sorting and enrichment.

B cell clones meeting the criteria were collected to prepare monoclonal antibodies. The WB detection result of a PD-L1 monoclonal antibody prepared according to the method is shown in FIG. 4. A membrane was prepared with a positive cell lysate NCI-H226 and a negative cell lysate for the PD-L1, and the protein loading quantity of the two lysates both was 40 μg/lane. According to the result in the figure, a clear band at 40-60 KDa can be observed on the NCI-H266 membrane by probing of PD-L1 B cell clone supernatant, while no blotting bands on the MCF-7 membrane. The result shows that the monoclonal antibody prepared by enrichment and sorting with the anti-biotin antibody by the magnetic bead method has excellent specificity.

Free biotin is often presented in the culture medium. The anti-biotin antibody-conjugated magnetic beads described in the experiment have the advantage of not binding to free biotin. The feature provides the most sensitive labeling and cell isolation. The anti-biotin antibody-conjugated magnetic beads provide an ideal solution for the isolation of specific cells, and can even separate cells from samples rich in debris or other rare biological materials.

The embodiments of cell capture, sorting and enrichment, and monoclonal antibody preparation by the flow cytometry method are as follows:

The anti-biotin antibody was cross-linked to a fluorescein to obtain an anti-biotin antibody-fluorescein. The anti-biotin antibody-fluorescein was filtered with a 0.22 μm filter membrane and stored at 4° C. for later use.

Biotin was cross-linked to a peptide or a protein in a proper way to obtain a biotinylated polypeptide/protein complex (biotin-Y). The biotinylated polypeptide/protein complex (biotin-Y) was filtered with a 0.22 µM filter membrane and stored at −20° C. for later use.

Lymphocytes from animals immunized with antigen Y were taken, and the biotin-Y complex was added. The lymphocytes were incubated at 4-37° C. for 1-120 min, or a longer time accordingly, cells were washed with DPBS or a culture medium several times, and the supernatant was removed by centrifugation.

The washed cells were resuspended in DPBS or the culture medium, and a certain amount of anti-biotin antibody-fluorescein and/or other antibodies, such as anti-CD19 antibody, anti-CD138 antibody and anti-IgG antibody were added. The mixture was mixed at 4-37° C. for 1-120 min, or incubated for a longer time accordingly, cells were washed with DPBS or the culture medium several times, and the supernatant was removed by centrifugation. The cells were resuspended, with an appropriate amount of DPBS or culture medium, to be loaded for flow cytometry.

Negative gating is set by the cells without the anti-biotin antibody fluorescein, then cells labeled with the anti-biotin antibody fluorescein are loaded to the sorter. Finally, cells are collected to the tube by combination of the signals of anti-CD19, anti-CD138 and anti-IgG antibodies.

After the cells were counted, the cells were adjusted to a suitable concentration and inoculated into a cell culture plate or culture dish, and the cell culture plate or culture dish was supplemented with sufficient culture medium.

The cells were cultured for several days and then the supernatant was taken for detection.

Figure 5:
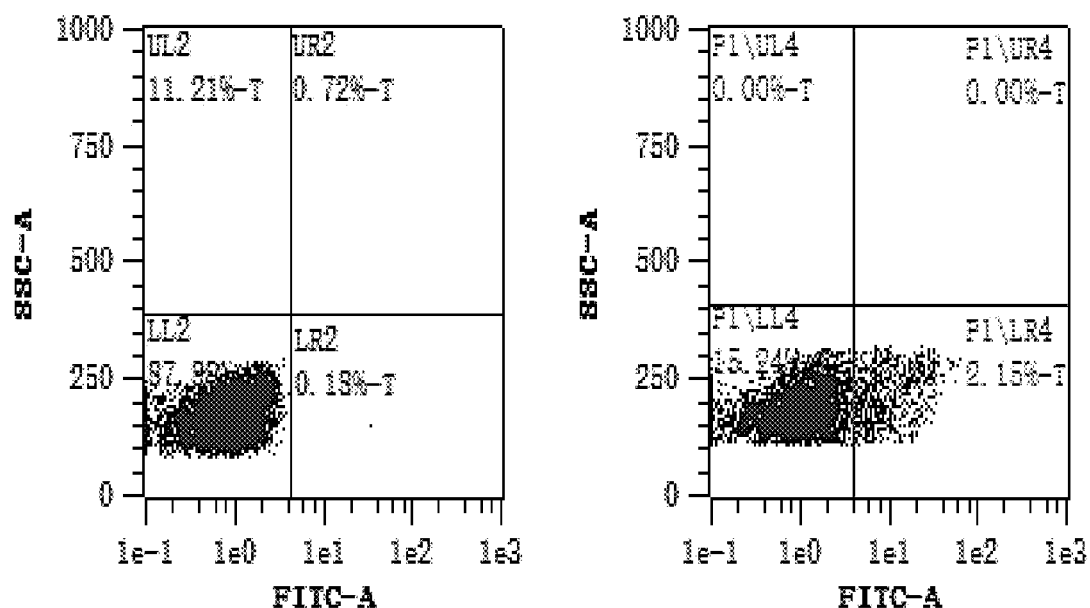
FIG. 5 is a picture of flow cytometry sorting results of immunized rabbit PBMCs labeled with an anti-biotin antibody.

B cell clones meeting the criteria were collected for monoclonal antibody generation. As shown in FIG. 5, the anti-biotin antibody was used for fluorescein activated cell sorting. The left picture shows the control group (without addition of the anti-biotin antibody-FITC), and the right picture shows the experimental group (with addition of the anti-biotin antibody-FITC). After the test, the control group had about 0.18% background cells, and the experimental group had 1.97% specific lymphocytes that could be sorted out for monoclonal antibody preparation. So, monoclonal antibodies can be generated by FACs using the fluorescein labeled anti-biotin antibody, which makes the monoclonal antibody generation more effective.

Free biotin is often presented in the culture medium. The fluorescein labeled anti-biotin antibody described in the experiment has the advantage of not binding to free biotin. The fluorescein labeled anti-biotin antibody provides an ideal solution for cell isolation by FACs.

Example 5: Western Blotting

The biotin conjugate biotin-X was loaded to an SDS-PAGE at 2 ng/lane for electrophoresis.

The prepared gel was then transferred onto a PVDF membrane.

After the PVDF membrane was activated with methanol, the PVDF membrane was blocked with 5% skimmed milk powder/PBS at room temperature for about 1 h. 2 µL of 0.5 mg/mL free D-biotin was mixed with 1:2000 and 1:5000 prediluted anti-biotin antibodies (the original concentration of the antibody was 0.500 mg/mL) and incubated at 30° C. for about 40 min, then the membrane was rinsed 3 times with TBST, and then the membrane was washed with TBST for about 10 min.

One lane of the PVDF membrane was probed with 75 µL of the complex of the antibody and free D-biotin, and another lane was probed with 75 µL of the anti-biotin antibody only, and incubated at room temperature for 1 h on a shaker, After the incubation, the membrane was washed twice with TBST for about 10 min each.

The 1:4000 prediluted goat anti-rabbit IgG-HRP secondary antibody was added, and incubated at room temperature for 1 h on a shaker. The membrane was washed 3 times with TBST for about 10 min each.

1.5 mL of ECL was added to each membrane. The membranes were allowed for coloration for 5 min at room temperature, and then the signal was read in an imager by exposure for 60 s.

Figure 6:
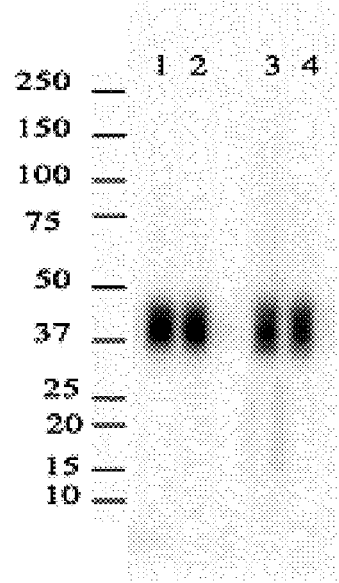
FIG. 6 is a picture of western blotting results of an anti-biotin antibody.

The picture taken by the gel imager is shown in FIG. 6. Lanes 1, 2, 3 and 4 indicate that the antibody can react with conjugated biotin, and show a single band with the size of about 45 kD. Lane 2 shows that the antibody does not react with free biotin, but only reacts with biotin conjugated to protein X on the PVDF membrane, and the band size and position have no significant difference compared with lane 1. Lane 4 shows that the antibody does not react with free biotin, but only reacts with biotin conjugated to protein X on the PVDF membrane, and the band size and position have no significant difference compared with lane 3.

Example 6: Flow Cytometry

Hela cells were washed with PBS, and centrifuged at 1500 rpm for 5 min at 4° C., and the cell density was adjusted to 3 M/mL.

100 µL of 4% paraformaldehyde solution was added to 1 M cells and mixed gently. The cells were fixed at room temperature for about 10 min.

PBS was added to stop fixation, the cells were centrifuged at 1500 rpm for 5 min, and the supernatant was discarded. Cell pellets were resuspended and washed with PBS, then the cells were centrifuged at 1500 rpm for 5 min again.

100 µL of 0.1% TritonX-100 (2-[4-(2,4,4-trimethylpentan-2-yl)phenoxy]ethanol) was added to 1 M cells, and mixed gently. Then cells were incubated at room temperature for about 15 min to permeabilize cell membrane.

The step (3) was repeated to wash the cells.

3 clean 1.5 mL centrifuge tubes were prepared and 100 µL of 3 M/mL Hela cells were added to each tube, that is, each tube contains 0.3 M Hela cells. After centrifugation, the supernatant was discarded. 100 µL of PBS was added to one tube as a negative control, 100 µL of 1:200 biotin-conjugated anti-cytokeratin 8 (CK8) rabbit monoclonal antibody was added to another tube, 100 µL of 5 µg/mL rabbit isotype IgG was added to the third tube, and all cells were incubated at room temperature for about 1 h.

The step (3) was repeated to wash the cells.

100 µL of the 1:100 prediluted FITC-labeled anti-biotin antibody was added to each tube. The step (3) was repeated to wash the cells after incubation at room temperature for 40 min, and 200 µL of PBS was added to each tube to detect the fluorescein intensity of the cells in each tube on a flow cytometer.

Figure 7:
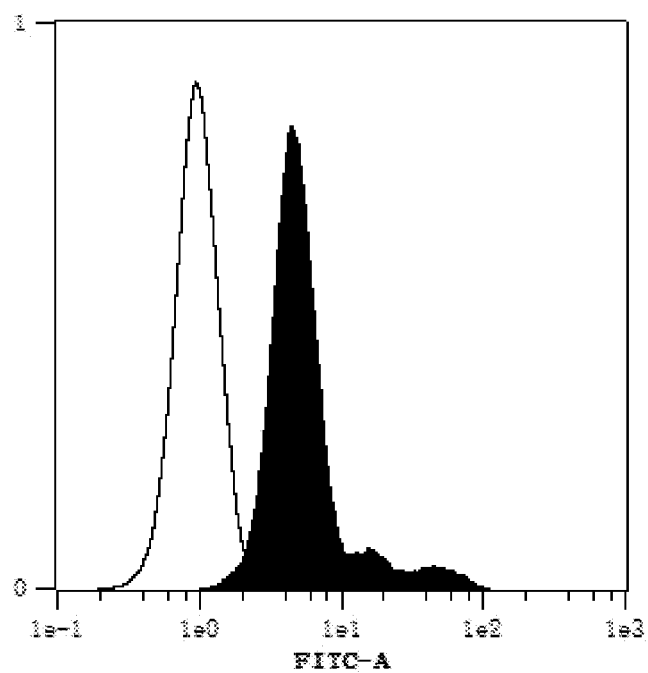
FIG. 7 is a picture of results of flow cytometry application of an anti-biotin antibody.

The results are shown in FIG. 7. The unfilled black histogram on the left is the isotype control group indicating that the Hela cells detected by isotype IgG-biotin conjugate and the FITC-labeled anti-biotin antibody. The histogram filled with black on the right is the experimental group indicating that the Hela cells detected by the anti-cytokeratin 8-biotin conjugate and the FITC-labeled anti-biotin antibody. From the figure, it can be seen that the peak of the experimental group shifts more to the right than the isotype control group, indicating that the anti-biotin antibody can be used in flow cytometry experiments.

Example 7: Immunofluorescent Staining

Hela cells grown in a 12-well plate at confluency of 50%-60% were washed twice with PBS.

1 mL of 4% paraformaldehyde solution was added to each well, and allowed to stand at room temperature for about 30 min for fixation.

The fixative solution was poured out. 1 mL of 1% BSA/PBST was added to each well. The cells were washed on a shaker for about 5 min, and then the washing solution was poured out. The step was repeated twice.

1 mL of 0.1% TritonX-100 (2-[4-(2,4,4-trimethylpentan-2-yl)phenoxy]ethanol) was added to each well. Then cells were incubated at room temperature for about 10 min to permeabilize cell membrane. The step (3) was repeated to wash the cells.

1 mL of 10% goat serum was added to each well and incubated at room temperature for about 30 min to block non-specific antigen sites on cells. The step (3) was repeated to wash the cells.

1 mL of 1% BSA/PBST was added to one well as a negative control, 1 mL of 1:200 biotin-conjugated anti-cytokeratin 8 rabbit monoclonal antibody was added to another well, 1 mL of 5 μg/mL rabbit isotype IgG antibody was added to the third well, and the cells were incubated at room temperature for about 1 h.

The step (3) was repeated to wash the cells. 1 mL of the 1:100 prediluted FITC-labeled anti-biotin antibody was added to each well. The cells were incubated at room temperature for about 50 min and then step (3) was repeated to wash the cells.

A drop of antifade mounting solution with DAPI was added on a blank glass slide. A cell slide was carefully clamped out of a well with tweezers. Then the cell slide (the side with the cells) was covered to the mounting solution, and let dry at room temperature in dark.

The slide was observed under a fluorescence microscope, and photos were taken.

Figure 8:
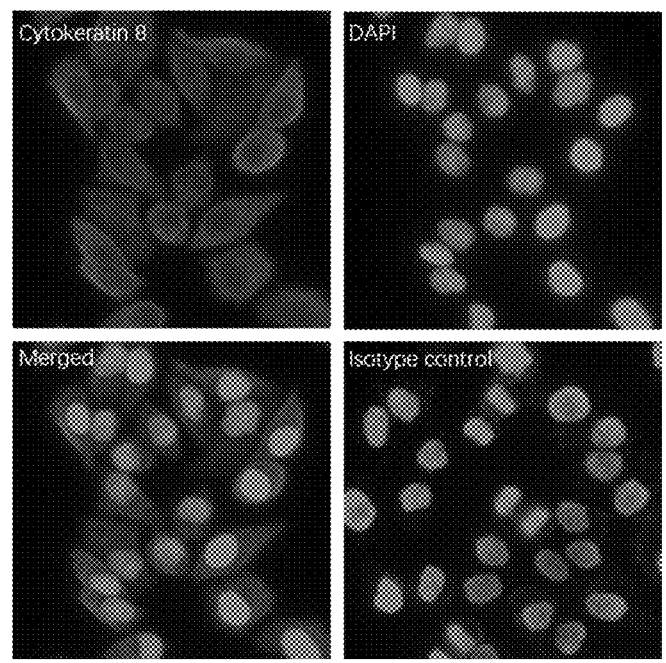
FIG. 8 is a picture of results of immunocytochemistry application of an anti-biotin antibody.

The results are shown in FIG. 8. There are 4 small pictures in the figure. The picture in the upper left corner shows the signal of anti-cytokeratin 8 monoclonal antibody at 1:200 dilution. The picture was taken with a green fluorescein channel to locate the cytokeratin 8 protein in the cytoplasm. The picture in the upper right corner shows the signal of anti-cytokeratin 8 monoclonal antibody at 1:200 dilution, and the picture was taken with a blue fluorescein channel to locate the cell nucleus. The picture in the lower left corner shows the merged signal of the green and blue channel. The picture in the lower right corner shows the merged signal of negative control. It can be seen that only the anti-CK8 antibody showed green cytoplasma staining signal. The anti-biotin antibody can be used in immunofluorescent staining experiments.

Example 8: Immunohistochemistry

Human endometrium tissue was selected for CK-8 staining in IHC experiment.

The endometrium tissue slides were fixed in an oven at 62° C. for about 1 h.

Tris-EDTA (pH 9.0) was used for antigen retrieval.

100 μL of the 1:50 prediluted biotin-conjugated anti-cytokeratin 8 rabbit monoclonal antibody was added to the slides. The slides were incubated at room temperature for about 30 min, and then washed.

The 1:100 prediluted HRP labeled anti-biotin antibody was added to the slides. The slides were incubated at room temperature for about 30 min, and then washed.

100 μL of DAB was added. Color was developed at room temperature for about 2 min, and the slides were rinsed with water.

The slides were put into a hematoxylin staining solution for 2 min to stain the nucleus and then washed with water. Then the slides were put in PBST to return to blue for 60 s.

After dehydration and transparency, the slides were mounted and let dry in a fume hood. The slides were photographed under a microscope.

Figure 9:
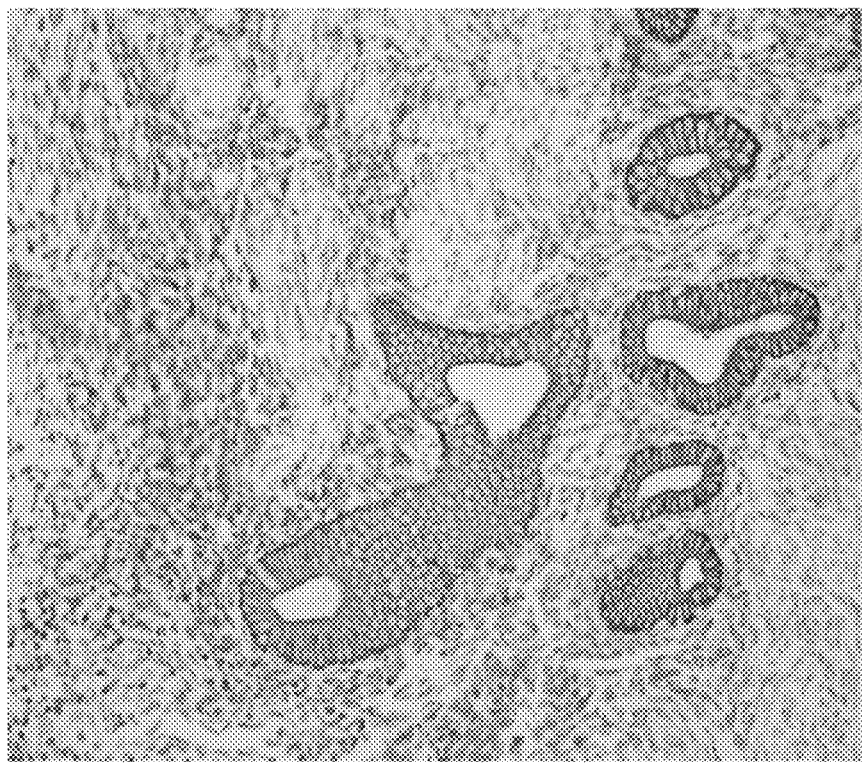
FIG. 9 is a picture of results of immunohistochemistry application of an anti-biotin antibody.

The results are shown in FIG. 9. In the figure, cytokeratin 8 has specific cytoplasmic staining on the glandular epithelium of the endometrium. The staining result is located correctly, and no non-specific staining and background staining are presented. The antibody can be used in immunohistochemistry experiments.

The invention claimed is:

1. An anti-biotin antibody, wherein the antibody includes complementary determinant regions (CDR) of a heavy chain and a light chain, the heavy chain of the antibody includes three complementary determinant regions including CDR-H1, CDR-H2, and CDR-H3, and the light chain of the antibody includes other three complementary determinant regions including CDR-L1, CDR-L2 and CDR-L3, the CDR-H1, the CDR-H2, the CDR-H3, the CDR-L1, the CDR-L2 and the CDR-L3 of the antibody comprising the following polypeptide sequences:

(1) the CDR-H1 comprising at least 6 amino acid sequences of SEQ ID NO: 1, the sequence being SSYWIC;

(2) the CDR-H2 comprising at least 18 amino acid sequences of SEQ ID NO: 2, the sequence being CIDAGSSGSTYYARWVNG;

(3) the CDR-H3 comprising at least 14 amino acid sequences of SEQ ID NO: 3, the sequence being EGDWGAPIYYGVDL;

(4) the CDR-L1 comprising at least 13 amino acid sequences of SEQ ID NO: 4, the sequence being QSSQSVYNNNQLS;

(5) the CDR-L2 comprising at least 7 amino acid sequences of SEQ ID NO: 5, the sequence being YASTLAS;

(6) the CDR-L3 comprising at least 12 amino acid sequences of SEQ ID NO: 6, the sequence being LGGYYDYADTSA, wherein, the anti-biotin antibody specifically binds to non-free biotin.

2. The anti-biotin antibody of claim 1, wherein the antibody is a rabbit monoclonal antibody.

\* \* \* \* \*